United States Patent [19]

Pignataro

[11] Patent Number: 5,584,884
[45] Date of Patent: Dec. 17, 1996

[54] MAMMARY PROSTHESIS AND METHOD OF SURGICALLY IMPLANTING SAME

[75] Inventor: Anthony S. Pignataro, 119 Carla La., West Seneca, N.Y. 14224

[73] Assignee: Anthony S. Pignataro, West Seneca, N.Y.

[21] Appl. No.: 508,223

[22] Filed: Jul. 27, 1995

[51] Int. Cl.⁶ ............................................. A61F 2/12
[52] U.S. Cl. .................. 623/8; 623/11; 606/151
[58] Field of Search ................. 623/8, 11, 66; 606/151, 213, 215

[56] References Cited

U.S. PATENT DOCUMENTS

| | | | |
|---|---|---|---|
| 3,054,406 | 9/1962 | Usher | 606/151 |
| 4,372,293 | 2/1993 | Vijil-Rosales | 128/1 |
| 4,840,629 | 6/1989 | Bustos | 623/8 |
| 5,282,856 | 2/1994 | Ledergerber | 628/8 |
| 5,334,217 | 8/1994 | Das | 606/151 |
| 5,368,602 | 11/1994 | de la Torre | 606/151 |
| 5,433,996 | 7/1995 | Kranzler et al. | 623/11 |
| 5,441,508 | 8/1995 | Gazielly et al. | 606/151 |
| 5,507,811 | 4/1996 | Koike et al. | 606/151 |

FOREIGN PATENT DOCUMENTS 2682284  4/1993  France.

OTHER PUBLICATIONS

Bustos, Ricardo A., M.D.; Periareolar Mammaplasty with Silicone Supporting Lamina; *Plastic and Reconstructive Surgery*, vol. 89, No. 4, Apr. 1992, pp. 646–657.

*Primary Examiner*—John G. Weiss
*Assistant Examiner*—Bruce E. Snow
*Attorney, Agent, or Firm*—Bean, Kauffman & Spencer

[57] ABSTRACT

A mammary prosthesis is disclosed as comprising a wedge shaped sheet of flexible biocompatible material having reinforced upper and lower attachment portions for attachment to bone of a patient by bone anchors, with the lower attachment portion being anchored to one or more ribs. The lower attachment portion includes a support member less flexible than the sheet material having suture receiving openings for receiving bone anchor sutures. A method of surgically implanting the mammary prosthesis is also disclosed.

9 Claims, 2 Drawing Sheets

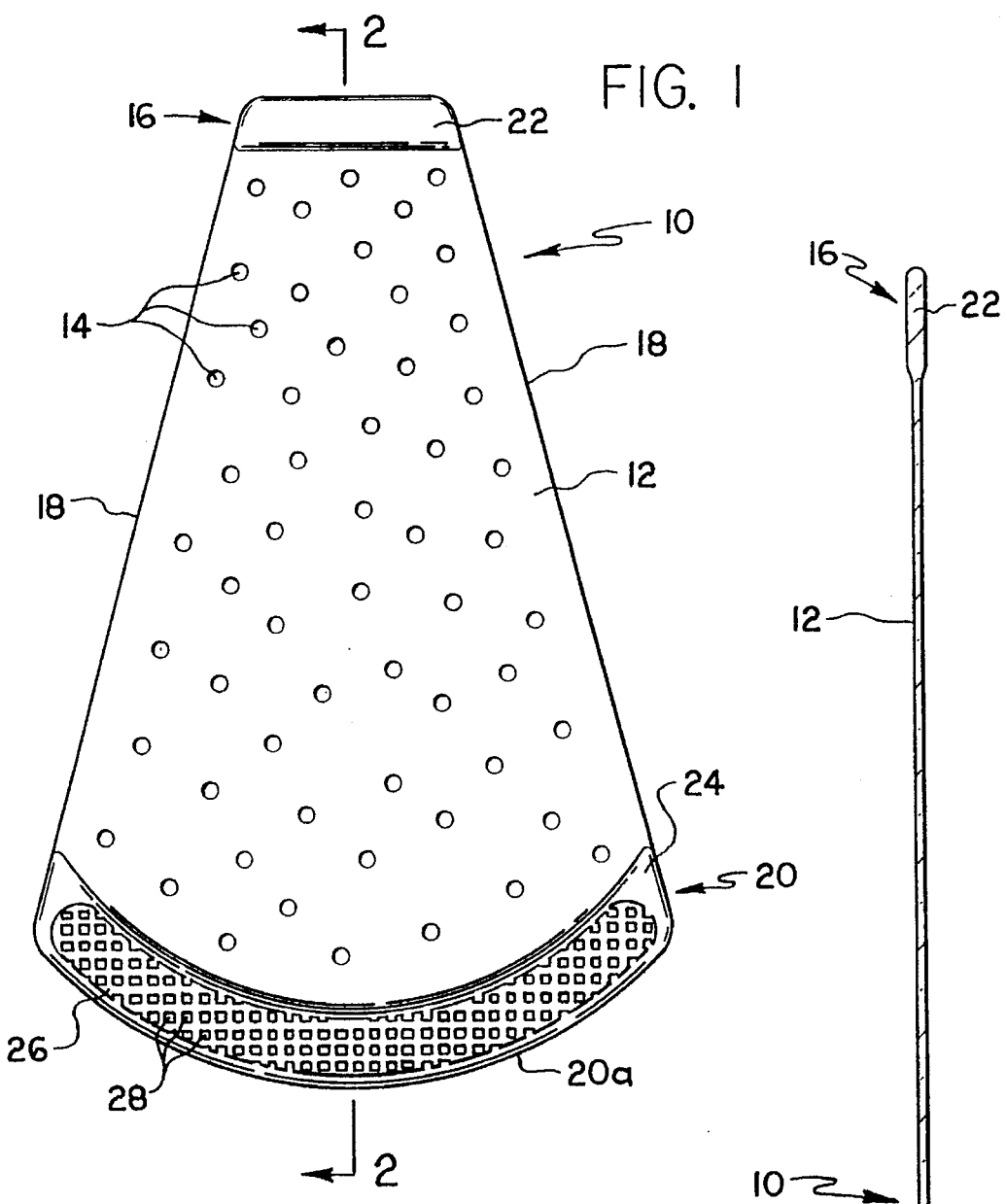
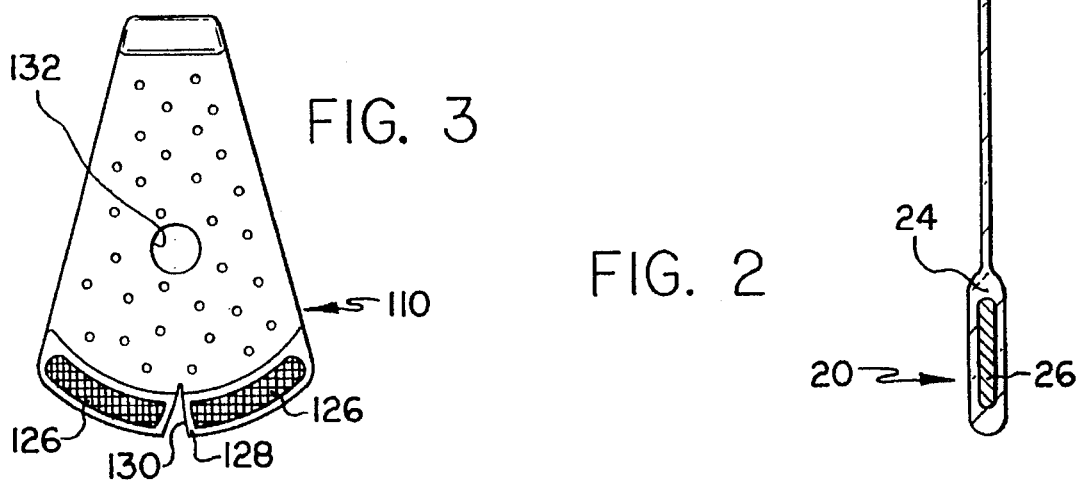

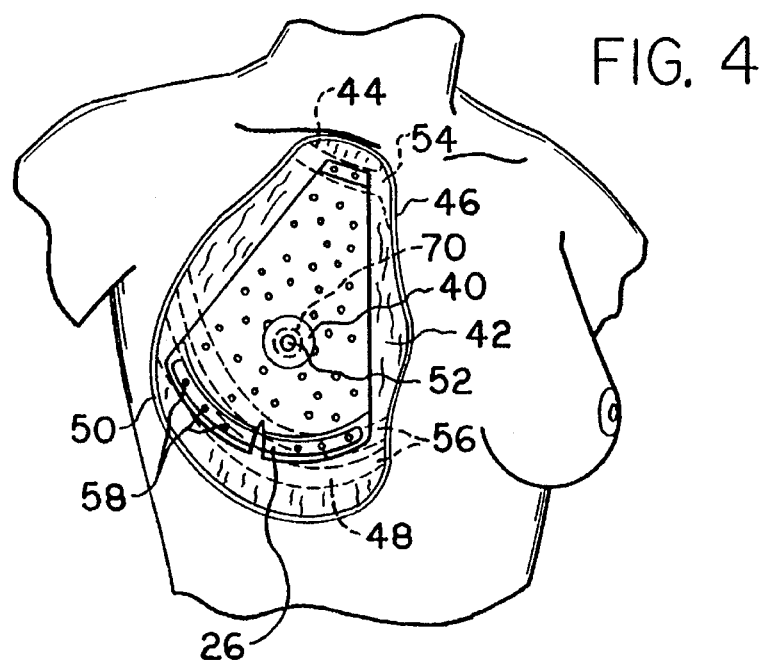
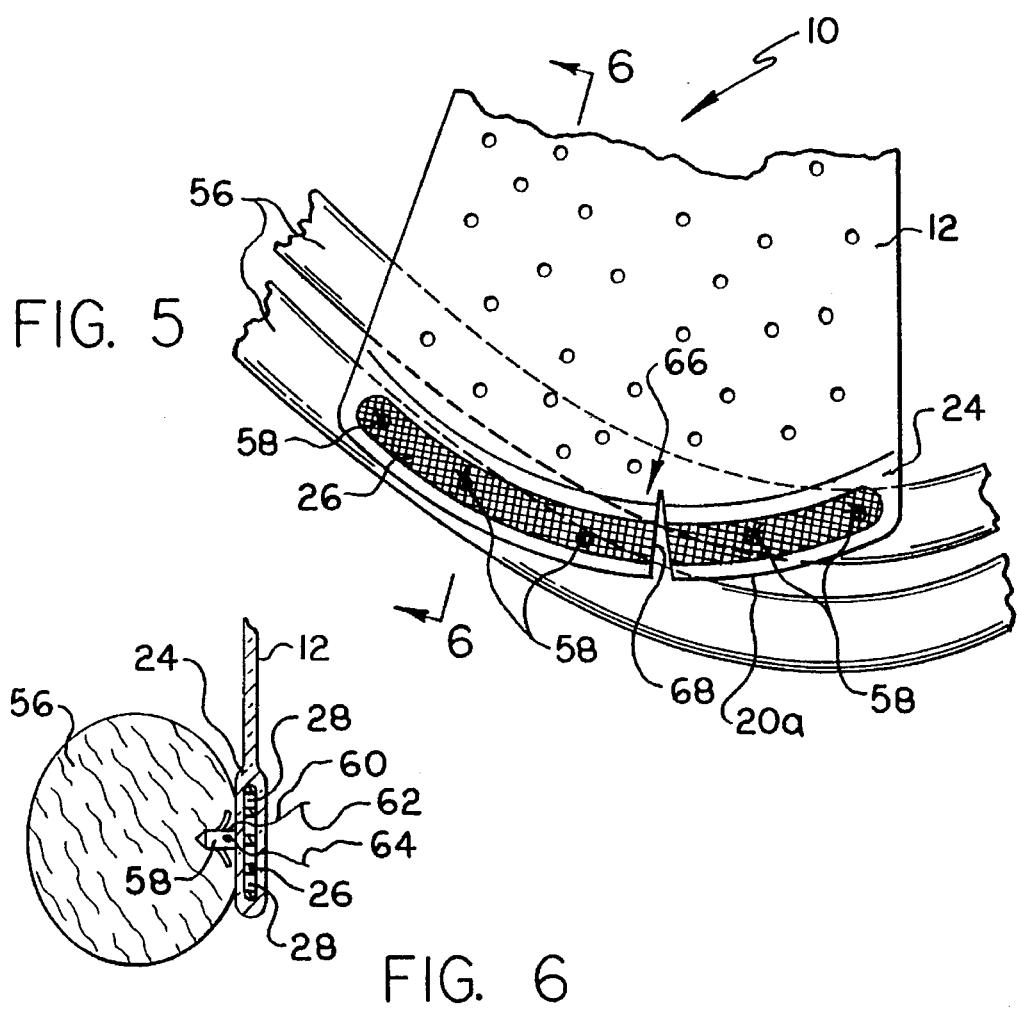

MAMMARY PROSTHESIS AND METHOD OF SURGICALLY IMPLANTING SAME

BACKGROUND OF THE INVENTION

A. Field of the Invention

The present invention relates generally to medical prostheses and methods of implanting same in a body of a patient, and more particularly to a subdermal mammary prosthesis for supporting breast tissue and a method of anchoring the mammary prosthesis to bone of a patient.

B. Description of the Prior Art

Efforts to surgically correct for breast ptosis, commonly known as sagging, and breast hypertrophy have heretofore involved implanting a flexible biocompatible sheet subdermally in contact with the breast tissue and attaching the sheet by sutures to muscle tissue to support and shape the breast tissue.

French Patent No. 2,682,284 to Dessart teaches a subdermal mammary prosthesis comprising a flexible collar having two asymmetrical branches which are fixed together at one point to form a frustoconical framework enveloping the breast and having an opening for the nipple and areola. The collar comprises a lower band sutured to muscle surrounding the breast tissue and an upper band sutured to the patient's pectoral muscles.

U.S. Pat. No. 4,840,629 to Bustos discloses a subdermal mammary prosthesis also comprising a flexible collar designed to surround the breast to form a frustoconical support or framework. The prosthesis includes a pair of outer peripheral projections at an upper boundary thereof to be sutured to the pectoral muscles of the patient for increasing the capacity of the prosthesis to support the breast tissue.

A shortcoming of the aforementioned prior art prostheses is that they are designed to be attached to muscle tissue of the patient. As a natural consequence of aging, muscle tissue loses its firm tone, thereby diminishing its capability to provide support for the breast tissue. Over time, ptosis will recur despite the implanted prosthesis.

SUMMARY OF THE INVENTION

Therefore, it is an object of the present invention to provide an improved mammary prosthesis which when implanted in a breast of a patient will shape and support the breast tissue for a greatly extended period of time relative to prior art mammary prostheses.

It is another object of the present invention to provide a mammary prosthesis designed to be anchored to bone of the patient.

It is a further object of the present invention to provide a mammary prosthesis which may be implanted using only a circum-areolar incision to minimize cosmetically undesirable scarring.

In brief summary, a mammary prosthesis formed in accordance with a preferred embodiment of the present invention comprises a generally wedge-shaped sheet of flexible biocompatible material having reinforced upper and lower attachment portions associated with narrow and wide ends thereof adapted for anchoring to bone of the patient. The lower attachment portion includes a support member, preferably formed of biocompatible metallic mesh, which is less flexible than the sheet.

By way of overview, a preferred method of implanting the mammary prosthesis includes making a circum-areolar incision in the breast, exposing the breast tissue, and dissecting the areolar skin off of the breast tissue to the nipple; positioning the prosthesis over the nipple and breast tissue; anchoring the lower attachment portion, and in particular the support member, to one or more ribs of the patient using bone anchors; anchoring the upper attachment portion to bone of the patient near the sterno-clavicular junction using bone anchors and tightening bone anchor sutures extending through the upper attachment portion to provide a desired supporting tension in the sheet; cutting a nipple opening through the sheet, pulling the nipple and areolar skin through the nipple opening and redraping the areolar skin in its natural position; and suturing the breast skin to the circumference of the areolar skin in its original position. If the support member is anchored to more than one rib, it must be cut at regions thereof extending between ribs to allow free mobility of the chest wall.

BRIEF DESCRIPTION OF THE DRAWINGS

The nature and mode of operation of the present invention will now be more fully described in the following detailed description taken with the accompanying drawings wherein:

FIG. 1 is a plan view of a mammary prosthesis formed in accordance with a preferred embodiment of the present invention;

FIG. 2 is a sectional view thereof taken generally along the line 2—2 in FIG. 1;

FIG. 3 is a plan view of a mammary prosthesis formed in accordance with an alternative embodiment of the present invention;

FIG. 4 is a cutaway view showing a mammary prosthesis formed in accordance with a preferred embodiment of the present invention implanted in a breast of a patient;

FIG. 5 is a partial view showing anchoring of a lower attachment portion thereof to more than one rib of a patient; and FIG. 6 is a sectional view taken generally along the line 6—6 in FIG. 5, however with bone anchor sutures in an untied condition.

DETAILED DESCRIPTION

Reference is initially directed to FIGS. 1 and 2 of the drawings, wherein a mammary prosthesis formed in accordance with a preferred embodiment of the present invention is illustrated and designated generally as 10. Prosthesis 10 is intended for subdermal surgical implantation in a breast of a female patient by methodology described hereinafter to provide support for the breast tissue to correct for breast ptosis and/or hypertrophy.

Prosthesis 10 comprises a sheet 12 of flexible, inert material having numerous perforations 14 throughout its entire area for enabling organic communication between the breast tissue and skin. Medical-grade silicone rubber sheeting available from Applied Biomaterial Technologies Corporation of Silverdale, Washington and sold under the trademark DURALASTIC® is suitable for practicing the present invention, however other biocompatible flexible sheeting products may of course be substituted therefor. It is desirable that sheet 12 be as thin as possible without compromising its effectiveness to support the breast tissue. A sheet thickness of 0.005 millimeters is contemplated as being sufficient for supporting breast tissue, however the thickness of sheet 12 may be chosen on a case by case basis. It is believed that sheeting ranging in thickness from 0.004 millimeters through 0.01 millimeters will function satisfactorily in a majority of cases.

Sheet 12 is in the general shape of a wedge having a narrow end 16 and side edges 18 diverging to a wide end 20 defined by a lower edge 20a which is preferably formed as an arc. It will be appreciated by those skilled in the art that various similar shapes may be used. Sheet 12 is reinforced to an increased thickness near narrow end 16 to provide an upper attachment portion 22 suitable for anchoring to bone of a patient as described hereinbelow. The increased thickness of upper attachment portion 22 serves to prevent tearing of sheet 12 at points where bone anchor sutures are passed through the upper attachment portion. A preferred thickness range for upper attachment portion is from 0.04 through 0.1 millimeters, however a suitable thickness may be determined on an individual case basis.

Sheet 12 is also reinforced to an increased thickness near wide end 20 to form a lower attachment portion 24 adapted to be anchored to one or more ribs of the patient inferiorly of the breast tissue, with a preferred thickness range corresponding to that set forth above with respect to upper attachment portion 22. Due to the flexibility of sheet 12, and in particular the tendency of sheet 12 to buckle or fold between points where bone anchor sutures pass through lower attachment portion 24, there is provided support means along lower attachment portion 24 in the form of a support member 26 less flexible than sheet 12 for permitting the lower attachment portion to follow and be anchored to one or more ribs while maintaining a relatively smooth topography of sheet 12.

In a preferred embodiment of the present invention, support member 26 comprises a unitary segment of titanium mesh arcuately shaped to correspond to arcuate lower edge 20a. Titanium mesh is known to be of suitable stiffness relative to sheet 12 to prevent buckling, and it is sufficiently malleable to allow an implanting physician to manipulate and bend support member 26 to locate the support member on one or more ribs and pass sutures therethrough during surgery, as described below. Where the anatomy of the patient requires that support member 26 be anchored to more than one rib, and most likely two ribs, support member 26 must be long enough to bridge across and be anchored to such ribs. As will be readily appreciated by those skilled in the art, apertures 28 in the mesh comprise a plurality of suture receiving openings through which bone anchor sutures may be passed during implant surgery. While titanium is specifically taught herein as a preferred material, other biocompatible metals may be used, and any biocompatible material exhibiting suitable properties with regard to support member 26 is considered to be an equivalent within the scope of the present invention.

Prosthesis 10 is preferably manufactured to be an integral unit, with support member 26 being embedded within reinforced lower attachment portion 24. It is contemplated to manufacture prosthesis 10 in a plurality of different sizes for selective fitting in accordance with the individual anatomy of the patient.

An alternative embodiment of the mammary prosthesis of the present invention is illustrated in FIG. 3 and identified generally by the reference numeral 110. In contrast to the above-described preferred embodiment having a unitary support member 26, the alternative embodiment depicted in FIG. 3 includes a pair of support members 126 disposed in end-to-end alignment and separated by a gap 128 between adjacent ends thereof. Each support member 126 is intended to be anchored to a separate rib of the patient. Gap 128 is intended to allow free mobility of the chest wall. In the event that a region of lower attachment portion 24 associated with gap 128 is not flexible enough to allow free mobility of the chest wall, a premade cut 130 may be provided in sheet 12 extending from lower edge 20a upward through gap 128 for the purpose of relieving constriction of the chest wall. In essence, gap 128 and optional cut 130 are features of alternative embodiment prosthesis 110 existing prior to surgical implantation, whereas such features are omitted from the preferred embodiment prosthesis 10 until they become necessary when support member 26 is anchored to more than one rib, in which case the implanting physician may add the features by making one or more cuts during surgical implantation as detailed below.

Alternative embodiment prosthesis 110 may optionally include a precut nipple opening 132 extending between opposite surfaces of sheet 12 through which the nipple and areolar skin may be passed during surgery. This differs from the preferred embodiment prosthesis 10, which lacks a nipple opening until one is provided by the implanting physician during surgery.

A preferred method of surgically implanting mammary prosthesis 10 according to the present invention will now be described with further reference to FIGS. 4–6. It will be understood that prior to surgery, the patient is fitted with an appropriately sized prosthesis bilaterally during pre-operative workup and evaluation.

After adequate anesthesia is achieved and with the patient sterily prepared and draped, a circum-areolar incision is made in the breast. The skin surrounding the areola 40 is repositioned to expose the breast tissue 42, preferably by elevating a skin flap superiorly to the clavicle 44, medially to the sternal border 46, and inferiorly to and following the seventh rib 48. The lateral dissection is carried out to the mid axillary line 50. Once breast tissue 42 is exposed, the areolar skin 40 is dissected off of the breast tissue to the limit of the nipple complex 52.

The pre-operatively sized prosthesis 10 is then positioned over breast tissue 42 so that a main vector of support is directed superiorly and medially towards the sterno-clavicular junction 54. This is achieved by situating lower attachment portion 24 inferiorly of nipple 52 in a position to support breast tissue 42, and situating upper attachment portion 22 superiorly and medially of nipple 52 in a location generally towards sterno-clavicular junction 54 relative to lower attachment portion 24.

The next step is to anchor lower attachment portion 24 to one or more ribs 56 of the patient. The rib or ribs beneath lower attachment portion 24 are palpated and a plurality of bone anchors 58 are installed therein at spaced intervals for connection generally along the extent of support member 26, with preferably at least two bone anchors per rib. A spacing interval of approximately one inch is sufficient in most instances, however anatomical particularities may dictate that other intervals be used. Where a single rib 56 is followed for a sufficient distance, three or more bone anchors may be required in such rib. Bone anchors 58, as depicted in FIG. 6, include a suture 60 having first and second ends 62 and 64 attached to respective suture needles (not shown) which are passed upward through lower attachment portion 24, and more particularly through separate suture receiving openings 28 in support member 26. Once all of the suture ends 62 and 64 have been passed through suture receiving openings 28, they may be securely tied to their opposite end to anchor lower attachment portion 24 in place. It is desirable that support member 26 be somewhat malleable to enable custom positioning thereof on the palpated rib or ribs 56.

With lower attachment portion 24 anchored in place, upper attachment portion 22 is anchored to bone generally proximate to sterno-clavicular junction 54 of the patient using two or more bone anchors 58. Respective suture ends 62 and 64 are passed through suture receiving openings (not shown) formed in upper attachment portion 22 by suture needles (also not shown) and tied using a sliding knot which permits tightening of suture 60 in a loop of selected length, thereby enabling the implanting physician to supply a suitable supporting tension or "lift" to sheet 12. The knots are then permanently secured.

At this point in the procedure, if lower attachment portion was anchored to more than one rib 56, an intra-operative chest X-ray is taken using a portable X-ray machine to generate an image of the chest area where lower attachment portion 24 is anchored. The generated X-ray image is used to determine a region or regions 66 of support member 26 extending between ribs 56 to which the support member is anchored. It is vital that support member 26 be divided at such regions 66 to maintain free mobility of the chest wall so as not to restrict breathing and other functions. A straight cut 68 extending from lower edge 20a through support member 26 is sufficient to achieve free mobility of the chest wall.

The implanting physician then provides a small round opening 70 approximately the size of nipple through sheet 12 at a position corresponding to a new position of nipple 52. Nipple 52 and previously dissected areolar skin 40 are pulled through nipple opening 70 and the areolar skin is redraped into its natural position.

Finally, the skin which had been repositioned to expose breast tissue 42 is returned to its natural position and sutured to the circumference of areola 40.

It should be understood that the above described procedure is intended to correct for breast ptosis. However, as will be appreciated by those skilled in the art, the above procedure may be modified to correct for breast hypertrophy, or a combination of hypertrophy and ptosis, as well. In such cases, resection of breast tissue 42 and mammary cone reconstruction may be undertaken using well known surgical techniques, and it is likely that a skin excision would become necessary to accommodate a smaller mammary cone.

What is claimed is:

1. A mammary prosthesis to be surgically implanted in a breast of a patient comprising:

a perforated flexible sheet having reinforced upper and lower attachment portions adapted for attachment to said patient, said lower attachment portion being arcuately shaped to substantially conform to an inferior border of said breast; and at least one malleable support member embedded within said lower attachment portion, said at least one support member being less flexible than said sheet and having a plurality of suture receiving openings forming a mesh pattern extending substantially throughout said at least one support member;

whereby a plurality of suture lengths may be passed through selected ones of said plurality of suture receiving openings and secured to a plurality of corresponding bone anchors to anchor said lower attachment portion to one or more ribs of said patient.

2. The mammary prosthesis according to claim 1, wherein said at least one support member comprises a unitary support member to be anchored to a single rib of said patient.

3. The mammary prosthesis according to claim 1, wherein said at least one support member comprises a unitary support member having a length sufficient to permit said support member to bridge across and be anchored to at least two ribs.

4. The mammary prosthesis according to claim 1, wherein said at least one support member comprises a plurality of support members disposed end to end in alignment.

5. The mammary prosthesis according to claim 1, wherein said at least one support member is formed of biocompatible metal mesh.

6. The mammary prosthesis according to claim 1, wherein said upper and lower attachment portions are integrally formed with said sheet.

7. The mammary prosthesis according to claim 1, wherein said prosthesis is in the general shape of a wedge having a narrow end and a wide end, said upper attachment portion being provided at said narrow end and said lower attachment portion being provided at said wide end.

8. The mammary prosthesis according to claim 1, wherein said sheet is from 0.004 mm through 0.01 mm thick, and said upper and lower attachment portions are thicker than said sheet.

9. The mammary prosthesis according to claim 1, further including a generally circular nipple opening through said sheet between said upper and lower attachment portions.

\* \* \* \* \*